United States Patent [19]

Hoskin et al.

[11] Patent Number: 4,671,283
[45] Date of Patent: Jun. 9, 1987

[54] FORCEPS

[75] Inventors: William J. Hoskin, Harpenden; Dermot J. Pierse, Brockham, both of England

[73] Assignee: Micra Ltd., Bedfordshire, England

[21] Appl. No.: 704,306

[22] Filed: Feb. 21, 1985

[30] Foreign Application Priority Data

Feb. 28, 1984 [GB] United Kingdom ............... 8405167

[51] Int. Cl.$^4$ ............................................. A61B 17/30
[52] U.S. Cl. ..................... 128/354; 128/355; 128/346
[58] Field of Search ................ 362/32; 128/354, 18, 128/334, 303; 40/547, 347

[56] References Cited

U.S. PATENT DOCUMENTS

| 1,094,575 | 4/1914 | Joutras | 128/18 |
|---|---|---|---|
| 2,376,448 | 5/1945 | Neugass | 128/354 |
| 3,287,547 | 11/1966 | Spedding | 128/354 |
| 3,578,973 | 5/1971 | Dooley | 40/547 |
| 3,614,414 | 10/1971 | Gores | 362/32 |
| 3,638,013 | 1/1972 | Keller | 362/32 |
| 3,766,376 | 10/1973 | Sadacca et al. | 40/547 |
| 4,302,797 | 11/1981 | Cooper | 362/32 |
| 4,524,647 | 6/1985 | Holoff | 128/354 |

Primary Examiner—Gene Mancene
Assistant Examiner—Wenceslao J. Contreras
Attorney, Agent, or Firm—Klein & Szekeres

[57] ABSTRACT

A pair of forceps has a shank and a pair of resilient arms. A groove, running along the inner face of each arm and communicating with a channel in the shank, accommodates a fiber optic cable which provides illumination at the tip of the forceps for items handled by the forceps. The use of the forceps is particularly suitable for manipulating an artificial lens in a human eye because the surface of the lens is illuminated to make it stand out against the liquid of the eye which has substantially the same refractive index as the lens.

11 Claims, 9 Drawing Figures

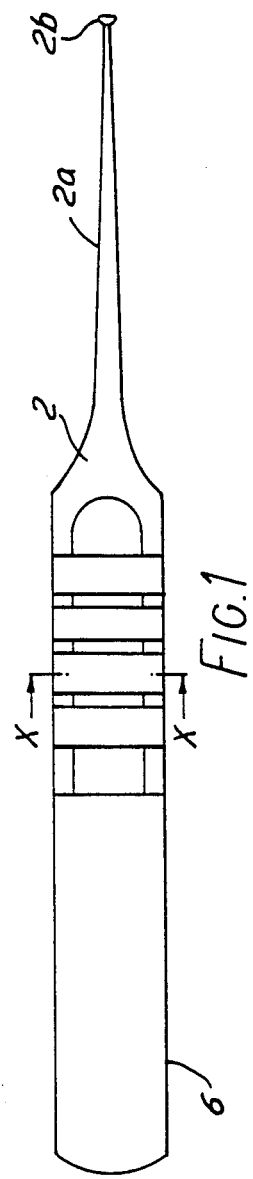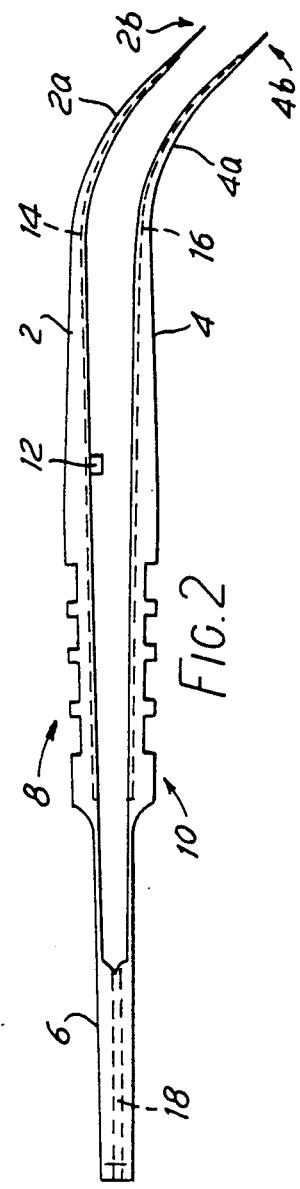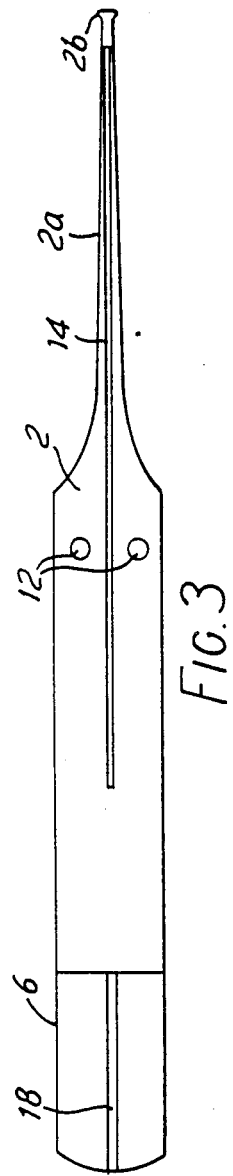

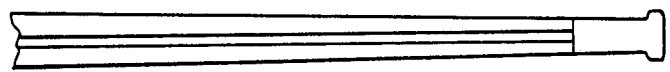
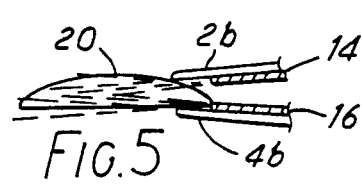
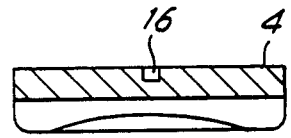
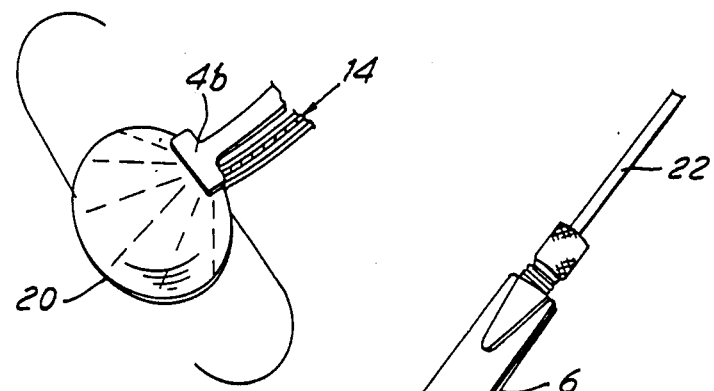
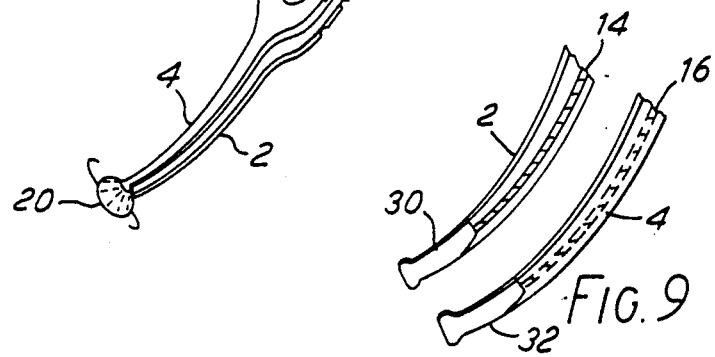

FORCEPS

BACKGROUND OF THE INVENTION

1. Field of the Invention

The present invention relates to forceps for use in opthalmic surgery, for example. More particularly, the present invention relates to surgical forceps which incorporate means for lighting the objects or work areas which are manipulated by the forceps.

2. Brief Description of the Prior Art

Conventional surgical forceps comprise a pair of resilient arms extending from a common shank. Such forceps are used for placement of an artificial lens on a human eye. Thereafter the forceps are used to manipulate the lens into the correct position within the eye. Because the lens usually has the same refractive index as the aqueous humour of the eye, it becomes very difficult to locate visually after its initial release from the forceps onto the eye and much time and effort may be wasted by the surgeon in locating it with the forceps in order to shift it into the correct position within the eye.

The present invention seeks to improve the locating of the lens by means of forceps.

SUMMARY OF THE INVENTION

According to the invention there is provided a pair of forceps having a shank, a pair of resilient arms extending from the shank, and a light conducting path extending from the shank to the free end portion of at least one arm, whereby when light is coupled to the path at the shank, any item handled by the forceps is illuminated by light emerging from the path at said free end.

BRIEF DESCRIPTION OF THE DRAWINGS

Forceps embodying the invention will now be described by way of example with reference to the accompanying drawings in which:

FIG. 1 is a plan view of the forceps;

FIG. 2 is a side elevation of the forceps of FIG. 1;

FIG. 3 is an underplan view of the upper arm of the forceps of FIG. 2;

FIG. 4 is a fragmentary view to an enlarged scale of the top end portion of the arm of the forceps of FIG. 3;

FIG. 5 is a fragmentary side elevation, to an enlarged scale, of the tip end portion of the forceps of FIG. 1 holding a lens;

FIG. 6 is a section of the lower arm of the forceps taken on line X—X in FIG. 1;

FIG. 7 is a perspective view of the forceps holding a lens;

FIG. 8 is a fragmentary view to an enlarged scale of the tip end of the forceps of FIG. 7; and FIG. 9 is a fragmentary perspective view showing a modification of the tips of the forceps.

DESCRIPTION OF THE PREFERRED EMBODIMENTS

The following specification taken in connection with the drawings sets forth the preferred embodiments of the present invention. The embodiments of the invention disclosed herein are the best mode contemplated by the inventors for carrying out their invention in a commercial environment, although it should be understood that several modifications can be accomplished within the parameters of the present invention.

The stainless steel forceps shown in FIGS. 1 to 3 has two arms 2,4 linked together by a shank portion 6 at one end, and having arcuate end portions 2a and 4a at the opposite end. Each end portion 2a and 4a terminates in an enlarged tip portion 2b and 4b.

Each arm 2,4 is provided with a respective series of ribs 8 and 10 providing finger gripping areas of the forceps. A pair of stops 12 are provided in the inner face of one arm 2 to limit the extent to which the arms can be moved towards one another.

A groove (14 and 16) is provided along the inner face of each arm (2 and 4). At the shank end of the forceps, the grooves 14 and 16 communicate with a common passage 18 extending through the shank 6. At the top end of the forceps each groove 14 and 16 terminates in a stepped portion formed on the inner face of the respective arms 2 and 4 (see FIG. 5).

Each groove houses a fiber optic cable (not shown). The ends of the two fiber optic cables emerging from the channel 18 in the shank are arranged to be coupled to a light source (not shown) through a fiber optic coupler 22 (see FIG. 7).

The terminating ends of the fiber optic cables at the tip end portions of the forceps are provided with an irregular surface so that when the tip end portions of the forceps engage a lens 20 (see FIG. 5), with the ends of the cables making physical contact with the lens, light transmitted by the cables will be coupled to at least one surface of the lens 20 to make it stand out against a background of the liquid of the eye.

In this way the whole surface of the lens 20 becomes readily distinguishable to a surgeon when he is attempting to position the lens within the eye.

The terminating end portions of the fiber optic cables at the tip end portions of the forceps can be arranged in a variety of different ways. These include tapering the end of each cable at an angle of 45° to the axis of the fiber, bending the fiber so that it is normal to the surface of the lens, or simply terminating the fiber with the end polished at right angles to the axis of the fiber. The liquid of the eye may be used to conduct the light from the fibers to the lens.

Instead of the optical fiber cables being located along the inner faces of the two arms of the forceps, they can be located along the outer faces of the two arms.

Instead of a single cable in each groove, a bundle of cables can be used.

In the modification shown in FIG. 9, the tip portion 30,32 of each arm 2,4 is of a transparent material molded into the arms 2,4. The cables are optically coupled to the tips 30 and 32 which may have their working surfaces roughened or otherwise made irregular so as to scatter the light emerging therefrom.

The material of the forceps and of the fiber optic cables are preferably heat resistant so as to withstand sterilization in an autoclave.

The forceps are arranged to be capable of handling double convex or aphatic lenses as well as plain or convex lenses.

Several further modifications of the invention may become readily apparent to those skilled in the art in light of the foregoing disclosure. Therefore, the scope of the present invention should be interpreted solely from the following claims.

We claim:

1. A pair of forceps having:
   a shank defining a channel;
   a pair of resilient arms extending from the shank, the inner face of at least one arm defining a groove;

a fiber optic cable accommodated in the channel and groove for defining a light conducting path extending from the shank to the free end portion of said at least one arm, the free end of said fiber optic cable defining an irregular surface so positioned and so orientated that when the forceps grips a translucent object, the surface contacts the object to effect a direct optical coupling with the object whereby when light is coupled to the cable at the shank, any translucent object handled by the forceps is injected with light.

2. Forceps according to claim 1 wherein the cable has a terminating end at the free end portion of the arm, which terminating end defines an irregular surface to scatter the light emerging therefrom.

3. Forceps according to claim 1 wherein each arm has a tip portion of transparent material rigid with the remainder of the arm and is optically coupled to said optical fiber cable.

4. Forceps according to claim 3 wherein each tip portion defines an irregular surface to scatter the light emerging therefrom.

5. A pair of surgical forceps for handling a lens comprising:
a shank defining a channel;
a pair of resilient arms extending from the shank, at least one arm defining a groove extending from the channel along the arm to the free end thereof;
a translucent tip portion rigid with the arm defining said groove, the working face of said tip portion defining an irregular surface for making contact with and for coupling light from the tip portion directly into a translucent object gripped by the forceps;
an optical coupler mounted on said shank, and
an optical conductor extending from said optical coupling along said channel and said groove into optically coupling arrangement with said tip portion, whereby when light is transmitted along said conductor, the surface of any lens which makes contact with the working face of the tip portion becomes illuminated.

6. A pair of surgical forceps according to claim 5 wherein the material of the forceps is of stainless steel.

7. A pair of surgical forceps comprising:
a pair of substantially resilient arms having a pair of gripping tip portions;
a shank body to which the resilient arms are operatively mounted, said shank body defining a channel;
an optical fiber accommodated in said channel and mounted to at least one of the resilient arms for conducting light to said tip portion of at least one of the resilient arms, said at least one tip portion defining an irregular surface positioned to make contact with and to couple light from said optical fiber directly into a translucent object gripped by the forceps; and
coupling means mounted to the shank for coupling the optical fiber to a light source, whereby light emitted from said at least one tip portion is injected directly into the translucent object.

8. The surgical forceps of claim 7 further comprising light source means operatively connected to the coupling means for providing light to the coupling means and to the optical fiber means.

9. The surgical forceps of claim 7 wherein the resilient arm includes a groove into which the optical fiber is mounted.

10. The surgical forceps of claim 7 including a further optical fiber mounted to the other of the said resilient arms.

11. The surgical forceps of claim 10 wherein the said other resilient arm includes a groove into which the said further optical fiber is mounted.

* * * * *